(12) United States Patent
Janssen et al.

(10) Patent No.: US 8,668,660 B2
(45) Date of Patent: Mar. 11, 2014

(54) ELECTROMECHANICAL SYSTEM FOR INTERPROXIMAL CLEANING

(75) Inventors: Jozef Johannes Maria Janssen, Herten (NL); Bart Gottenbos, Budel (NL); Mariska Hendriks-Van Rijsbergen, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 849 days.

(21) Appl. No.: 12/808,251

(22) PCT Filed: Dec. 9, 2008

(86) PCT No.: PCT/IB2008/055165
§ 371 (c)(1),
(2), (4) Date: Jun. 15, 2010

(87) PCT Pub. No.: WO2009/077919
PCT Pub. Date: Jun. 25, 2009

(65) Prior Publication Data
US 2010/0273126 A1    Oct. 28, 2010

Related U.S. Application Data

(60) Provisional application No. 61/014,487, filed on Dec. 18, 2007.

(51) Int. Cl.
*A61C 15/00* (2006.01)
*A61C 17/00* (2006.01)

(52) U.S. Cl.
USPC .............................. 601/162; 601/165; 433/80

(58) Field of Classification Search
USPC ......... 601/154, 155, 160, 161, 162, 165, 169; 433/80, 82, 89, 120
See application file for complete search history.

(56) References Cited

U.S. PATENT DOCUMENTS

| | | | |
|---|---|---|---|
| 5,033,961 A | 7/1991 | Kandler et al. | |
| 5,323,770 A | 6/1994 | Ito et al. | |
| 5,820,373 A | 10/1998 | Okano et al. | |
| 6,030,215 A | 2/2000 | Ellion et al. | |
| 6,159,006 A * | 12/2000 | Cook et al. | 601/165 |
| 7,147,468 B2 * | 12/2006 | Snyder et al. | 433/80 |
| 2002/0082545 A1 * | 6/2002 | Sennett et al. | 601/162 |
| 2006/0078844 A1 | 4/2006 | Goldman et al. | |
| 2007/0095942 A1 | 5/2007 | Ray et al. | |

FOREIGN PATENT DOCUMENTS

| | | |
|---|---|---|
| DE | 29909633 U1 | 10/1999 |
| EP | 1201201 A2 | 5/2002 |
| WO | 9948435 | 9/1999 |
| WO | 2005070324 A2 | 8/2005 |
| WO | 2005076818 A2 | 8/2005 |
| WO | 2006067760 A1 | 6/2006 |

* cited by examiner

*Primary Examiner* — Quang D Thanh

(57) ABSTRACT

The interproximal cleaning appliance includes a housing (12) and a spray applicator (16) extending therefrom for directing a spray of fluid droplets to the interproximal area. Within the housing is a spray-generating assembly (14) which includes a chamber, a movable piston (26) mounted therein, one-way inlets (42, 40) for gas and fluid and an outlet (44). A system (54) for moving the piston, such as a motor, operatively compresses a spring (32) which creates a partial vacuum in the chamber, allowing gas to flow into the chamber through the gas inlet. Release of the spring produces a stream of fluid droplets which flows out of the chamber through the applicator to the interproximal area.

13 Claims, 2 Drawing Sheets

US 8,668,660 B2

ELECTROMECHANICAL SYSTEM FOR INTERPROXIMAL CLEANING

TECHNICAL FIELD

This invention relates generally to the interproximal cleaning of teeth, and more specifically concerns a device which uses mechanical or electromechanical action to accomplish the cleaning.

BACKGROUND OF THE INVENTION

It is well known that regular flossing is important for good dental health. Flossing, which is directed toward cleaning of the interproximal area of the teeth, including cleaning below the gum line, reduces dental decay and gingivitis by removing plaque and food remnants in the interproximal area which are not typically reached by conventional brushing. However, even though flossing is highly recommended and produces consistent advantageous results, regular flossing is only done by a small minority of people. A large percentage of people (close to 50%) do not, in fact, floss at all.

While flossing has been shown to be the most effective means for interproximal cleaning, one alternative to flossing is a device which produces a stream of fluid droplets at high speed which are then directed into the interproximal area by a nozzle and/or guidance tip arrangement. This device uses a compressed gas, e.g. $CO_2$, cartridge to produce the fluid droplet stream. There are, however, recognized disadvantages to the use of compressed gas cartridges, including restrictions on air transport and the need to replace the cartridges on a regular basis. Further, gas cartridges have heat limitations, e.g. typically less than 49° C., which limits their use in certain environments and requires some oversight in the use and storage of the device and the gas cartridges.

Hence, while use of a stream of high-speed fluid droplets has been shown to be effective, it would be desirable to have such a fluid stream generated by means other than a gas cartridge, with relatively few, if any, restrictions on ordinary use.

SUMMARY OF THE INVENTION

An interproximal cleaning appliance, comprising: a housing; a spray-generating assembly positioned within the housing, the assembly including a hollow body member defining a chamber, having a movable piston-spring assembly positioned therein, a gas inlet with a one-way valve permitting gas to enter the body member, an inlet for fluid and an outlet for a spray of fluid droplets; and a system for moving the piston within the hollow body member, to compress the spring, wherein subsequent release of the piston following entry of gas and fluid into the chamber creates sufficient pressure within the chamber to produce a fluid droplet spray from the outlet which is directed to an applicator/nozzle assembly which extends from the housing for directing the fluid droplet spray to the interproximal area.

BEST MODE FOR CARRYING OUT THE INVENTION

Figure 1:
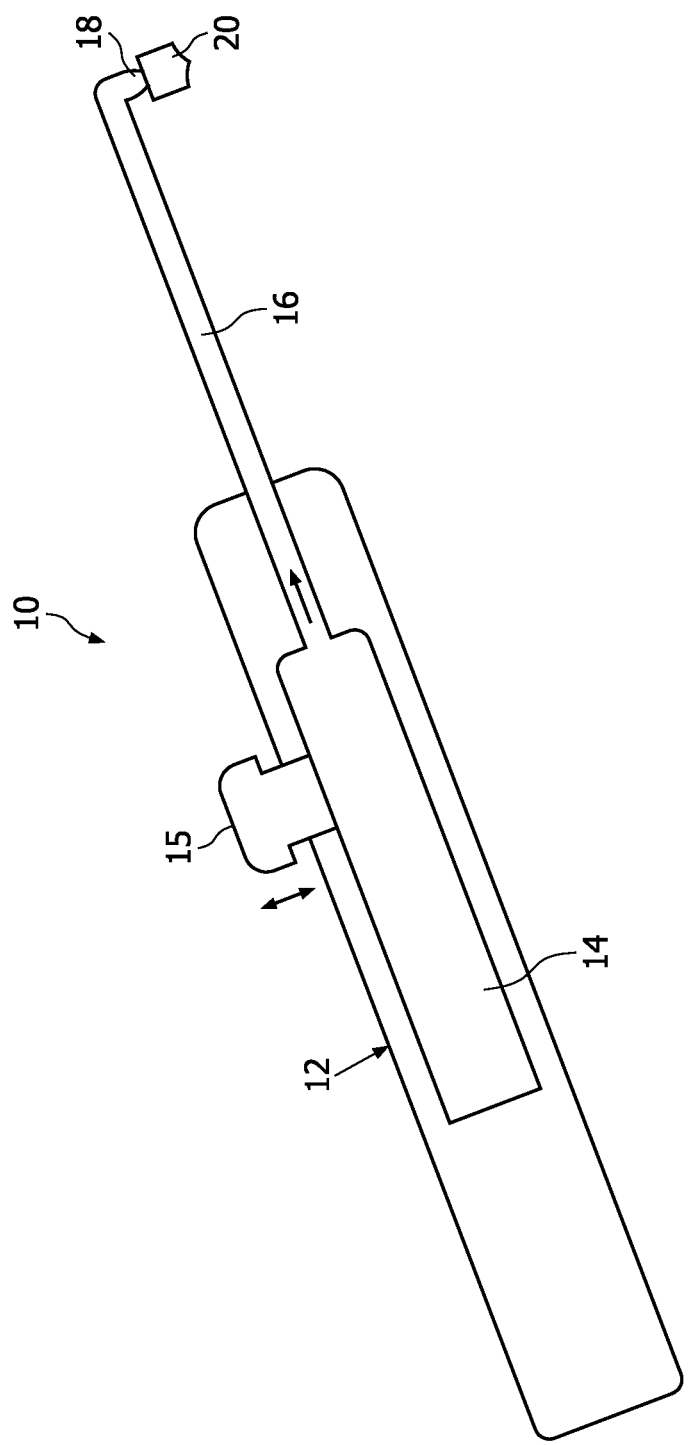
FIG. 1 shows a simplified schematic view of an interproximal cleaning device incorporating the present invention.

The figures illustrate an interproximal cleaning device which generates a stream of gas-propelled fluid droplets. A simplified view of a complete device 10 is shown in FIG. 1. It includes a housing 12, an internal assembly for creating the gas-propelled fluid stream 14, a user-operated control button 15 and an extended applicator 16 through which the fluid stream is directed. At the end of applicator 16 is a nozzle 18 through which the fluid droplets move into a guidance tip 20, which is configured to mate with the interproximal space of the teeth, thereby assuring that the fluid stream will hit the interproximal surfaces and clean them.

Housing 12 is configured to be conveniently held by a user and is further configured to accommodate the fluid stream generator 14. Generator 14 could also be a stand-alone unit tethered to the appliance. Generator 14 is a mechanical or electromechanical device for producing the fluid droplet stream. As such, it does not require a $CO_2$ or other compressed gas cartridge and thereby has none of the disadvantages of a compressed-gas based appliance.

Figure 2:
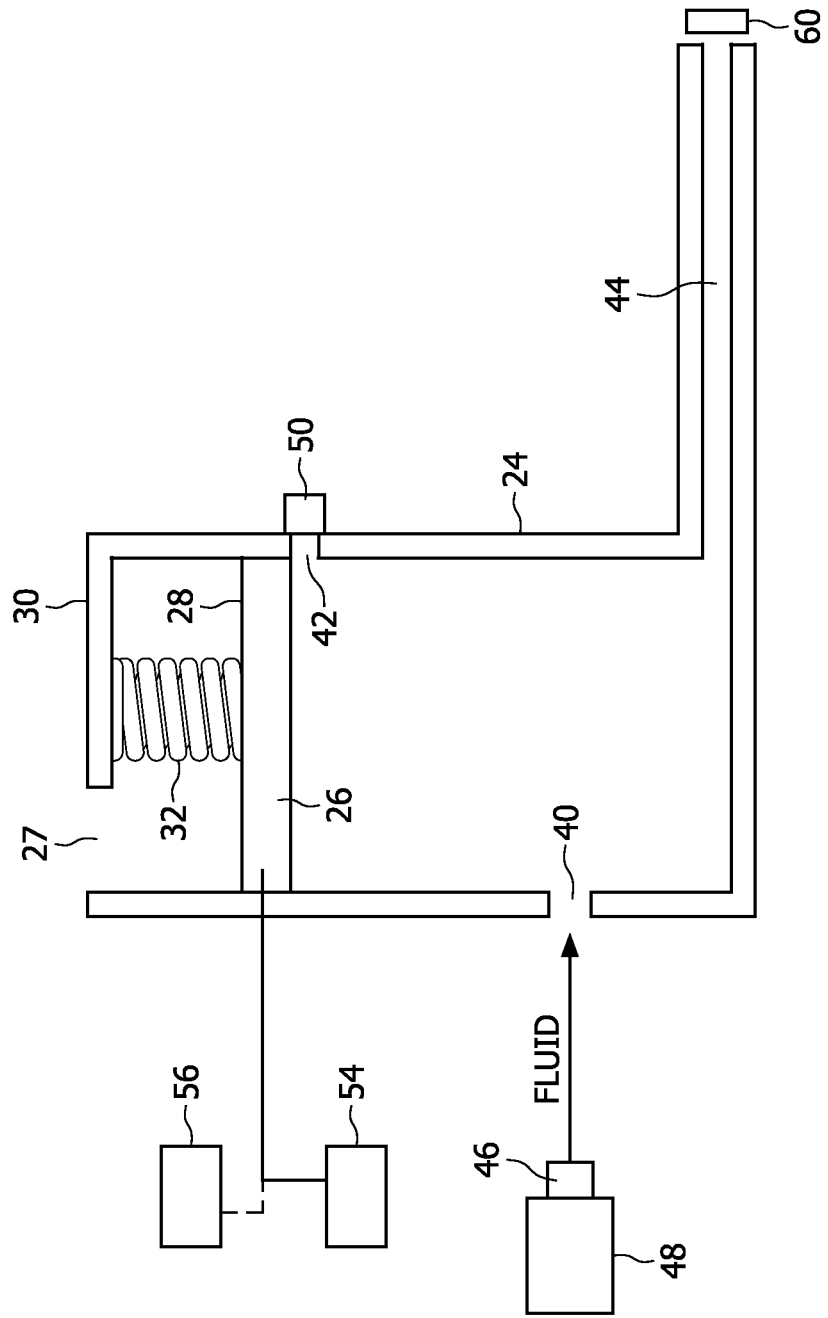
FIG. 2 is an enlarged view of an operative portion of the device of FIG. 1.

One embodiment of the generator is shown in FIG. 2 in simplified form. It includes a cylinder 24, which in the embodiment shown, is approximately 10 cm long and 2½ cm in diameter. Fitted into the cylinder in the upper portion thereof is a piston 26 which is adapted and configured to move up and down in cylinder 24. At the top of cylinder 24 is an opening 27, permitting communication between an upper portion of the internal volume of the cylinder and the atmosphere as the piston moves up and down in the cylinder. Connected between an upper surface 28 of piston 26 and a top portion 30 of cylinder 24 is a spring 32. Cylinder 24 also has a fluid inlet 40 and a gas inlet 42. Gas inlet 42 could also be located at the bottom of the cylinder. At the lower end of cylinder 24 is an outlet channel 44 through which the gas-propelled fluid droplet stream moves to the applicator 16.

In the embodiment shown, fluid inlet 40 is configured to allow water or other fluid, such as mouthwash or an antibacterial solution, in a typical amount of 0.1 ml-1 ml into the cylinder 24 for one operation of the appliance. Valve 46 controls the entry of fluid from a reservoir 48. Gas inlet 42 includes a one-way valve 50 which permits air or other gas to enter cylinder 24 but prevents the outflow of gas during movement of the piston. Valve 46 can also be a one-way valve. At the start of an operational cycle, spring 32 is not compressed, i.e. at rest, and piston 26 is also at rest, positioned below gas inlet 42. Piston 26 is then moved upwardly, compressing spring 32, either by a motor 54, a hand-operated wind-up mechanism 56 or other means. As piston 26 moves upwardly, a partial vacuum within cylinder 24 is created such that when gas inlet 42 is uncovered, air or other gas enters cylinder 24. One-way valve 50 prevents gas from escaping back to the atmosphere.

When piston 26 is released, it moves downwardly by the force of the compressed spring, which increases the pressure within the cylinder. The resulting high pressure, on the order of 10 bar, on the gas/fluid mixture in the interior volume of the cylinder is sufficient to create a high-speed spray of fluid droplets and direct it through outlet channel 44. This pressure can be varied, i.e. within a range of 5-60 bar. In the embodiment shown, the outlet channel has a diameter of 2½ mm, although the diameter could be less, down to 0.5 mm. Typically, in the embodiment shown, there will be no valve on the outlet channel, although a valve could be used. The fluid droplet stream is directed through the outlet channel to applicator 16, through nozzle 18 which forms the spray, and then out through guidance tip 20 to the interproximal area of the teeth, cleaning plaque and removing food remnants therefrom.

In an alternative embodiment, a motor or other means is used to move the piston downwardly from a rest position, after gas has been introduced into the cylinder, thereby pressurizing the cylinder, at approximately 10 bar, or in the range specified above. A valve 60 on the outlet channel maintains the pressure in the cylinder. When the piston is at its lowest position, with pressure maximum, the outlet valve is opened, resulting in a stream of fluid droplets being created and directed through the outlet channel and then through the applicator nozzle and the guidance tip into the interproximal area.

Hence, an interproximal cleaning device has been described and shown, which produces effective interproximal cleaning using a high-speed fluid droplet spray, without the need for a source of compressed gas.

Although a preferred embodiment of the invention has been disclosed here for the purposes of illustration, it should be understood that various changes, modifications and substitutions may be incorporated in the embodiment without departing from the spirit of the invention, which is defined by the claims which follow.

The invention claimed is:

1. An interproximal area cleaning appliance, comprising:
a housing;
a spray-generating assembly positioned within the housing, the assembly including a hollow body member defining a chamber, having a movable piston-spring assembly positioned therein, comprising a piston and a spring, wherein the spring extends between an upper surface of the piston and an upper end of the body member, a gas inlet into the chamber with a one-way valve permitting gas to enter the body member, a separate inlet for fluid into the chamber and an outlet from the chamber for a spray of fluid droplets; and
a system for moving the piston within the hollow body member from a rest position in which the gas inlet is blocked, to compress the spring, resulting in the piston being in another position in which the gas inlet is unblocked, wherein subsequent release of the piston, following entry of gas and fluid into the chamber, creates sufficient pressure within the chamber to produce a fluid droplet spray from the outlet which is directed to an applicator/nozzle assembly which extends from the housing for directing the fluid droplet spray to the interproximal area.

2. The cleaning appliance of claim 1, including a motor for moving the piston to compress the spring.

3. The cleaning appliance of claim 1, including a hand-operated mechanism for moving the piston to compress the spring.

4. The cleaning appliance of claim 1, including a valve on the outlet which is closed during compression of the spring and is opened to release the fluid droplet spray.

5. The cleaning appliance of claim 1, wherein the fluid entering the body member for each compression/release of the spring is an amount in the range of 0.1 ml-1 ml.

6. The cleaning appliance of claim 1, wherein the outlet has a diameter within the range of 0.5 mm-2½ mm.

7. The cleaning appliance of claim 1, including an opening in the upper end of the body member to outside the body member.

8. The cleaning appliance of claim 1, wherein the one-way valve prevents gas from escaping from the chamber.

9. The cleaning appliance of claim 1, wherein the pressure is within the range of 5-60 bar.

10. An interproximal area cleaning appliance, comprising:
a housing;
a spray-generating assembly positioned within the housing, the assembly including a chamber, a movable piston assembly positioned therein, a one-way inlet into the chamber for gas to enter the chamber, a separate inlet for a fluid into the chamber and an outlet from the chamber for a spray of fluid droplets, the outlet including a valve, normally in a closed position; and
a system for moving the piston assembly within the chamber from a rest position after gas and fluid have been introduced into the chamber, in a manner to increase pressure therein when the outlet valve is closed to produce a stream of fluid droplets which move from the chamber when the outlet valve is opened, the stream of droplets being directed to an applicator/nozzle member extending from the housing for directing the fluid droplet spray to the interproximal area.

11. The cleaning appliance of claim 10, wherein the pressure produced within the chamber prior to release is within the range of 5-60 bar.

12. The cleaning appliance of claim 10, wherein the piston spring piston assembly includes a motor for moving the piston assembly for increasing pressure within the chamber.

13. The cleaning appliance of claim 10, wherein the piston assembly includes a hand-operated mechanism for increasing pressure within the chamber.

* * * * *